US011633054B2

(12) United States Patent
Esser

(10) Patent No.: US 11,633,054 B2
(45) Date of Patent: Apr. 25, 2023

(54) MINDFULNESS ASSISTING ASSEMBLY AND METHOD

(71) Applicant: Stephanie Esser, Inver Grove, MN (US)

(72) Inventor: Stephanie Esser, Inver Grove, MN (US)

( * ) Notice: Subject to any disclaimer, the term of this patent is extended or adjusted under 35 U.S.C. 154(b) by 1076 days.

(21) Appl. No.: 16/354,330

(22) Filed: Mar. 15, 2019

(65) Prior Publication Data

US 2020/0288892 A1    Sep. 17, 2020

(51) Int. Cl.
*A47G 9/10* (2006.01)
*A47G 9/00* (2006.01)
*A61M 21/00* (2006.01)

(52) U.S. Cl.
CPC ........... *A47G 9/1045* (2013.01); *A47G 9/007* (2013.01); *A61M 21/00* (2013.01); *A61M 2021/0022* (2013.01); *A61M 2021/0044* (2013.01); *A61M 2205/586* (2013.01)

(58) Field of Classification Search
CPC .............................................. A61M 21/00–02
See application file for complete search history.

(56) References Cited

U.S. PATENT DOCUMENTS

| | | | |
|---|---|---|---|
| 4,670,924 A | 6/1987 | Spector | |
| 5,525,088 A | 6/1996 | Mayne | |
| 6,383,130 B1 * | 5/2002 | Wade | A61M 21/00 600/27 |
| 6,434,769 B1 | 8/2002 | Koenig | |
| 6,749,479 B2 | 6/2004 | Vick | |
| 2,198,942 A1 | 6/2010 | Gutierrez | |
| 2008/0032592 A1 | 2/2008 | Korbonski | |
| 2009/0149698 A1 * | 6/2009 | Tastard | A61M 21/00 472/133 |
| 2012/0028532 A1 | 2/2012 | Thompson | |
| 2015/0135442 A1 | 5/2015 | Deane | |
| 2015/0273178 A1 * | 10/2015 | Johnson | A61M 21/02 600/27 |
| 2016/0104389 A1 * | 4/2016 | Humphries | G09B 19/00 434/236 |
| 2017/0014595 A1 * | 1/2017 | Heath | G09B 1/00 |
| 2017/0319973 A1 * | 11/2017 | Perez | A47G 9/083 |
| 2018/0272102 A1 | 9/2018 | Grainger | |

FOREIGN PATENT DOCUMENTS

CA         2311342         12/2001

* cited by examiner

Primary Examiner — Thaddeus B Cox

(57) ABSTRACT

A mindfulness assisting assembly includes a housing that has a front wall, a rear wall and a perimeter edge defined at a juncture of the front and rear walls. The perimeter edge includes a first lateral edge, a second lateral edge, a top edge and a bottom edge. Each of the front and rear walls is comprised of a flexible material. The front and rear walls each comprise a cloth material and the front wall has a different tactile impression than the rear wall. A resiliently compressible material is positioned within the housing. A pair of grips is attached to the housing such that each of the first and second lateral edges has one the grips attached thereto.

6 Claims, 5 Drawing Sheets

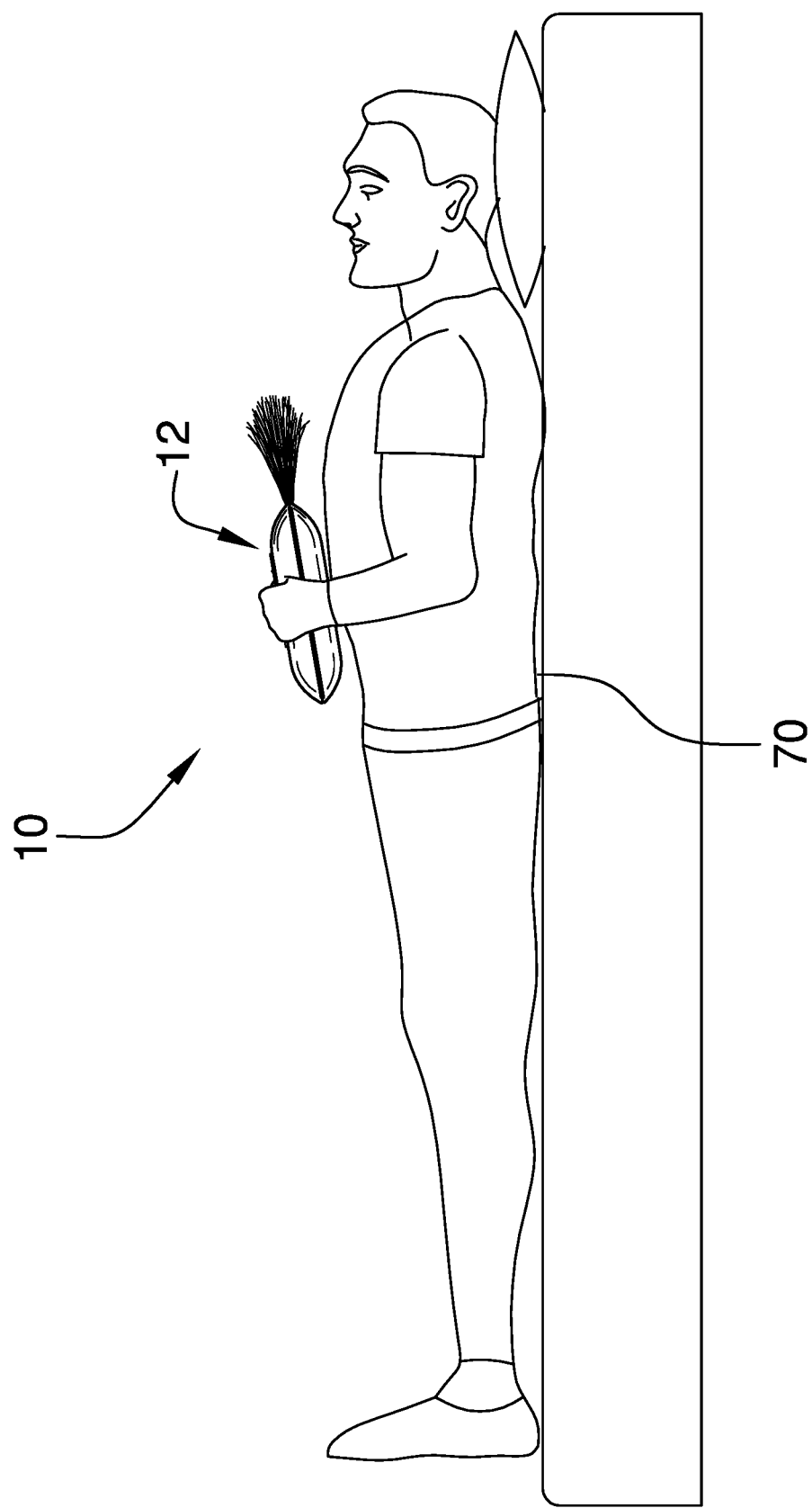

MINDFULNESS ASSISTING ASSEMBLY AND METHOD

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The invention relates to devices and systems which assist a person in achieving a state of mindfulness as well as promoting self-care and other benefits relating thereto.

(2) Description of Related Art Including Information Disclosed Under 37 CFR 1.97 and 1.98

The disclosure and prior art relates to meditation aid devices and more particularly pertains to a new meditation aid device for providing tactile, visual and olfactory stimulus to assist a person, and in particular a child, with remaining in a mindful state wherein the child is able to more easily focus on their current physical and emotional condition. The child thereby learns to draw their attention internally to promote self-regulation and resiliency.

BRIEF SUMMARY OF THE INVENTION

An embodiment of the disclosure meets the needs presented above by generally comprising a housing that has a front wall, a rear wall and a perimeter edge defined at a juncture of the front and rear walls. The perimeter edge includes a first lateral edge, a second lateral edge, a top edge and a bottom edge. Each of the front and rear walls is comprised of a flexible material. The front and rear walls each comprise a cloth material and the front wall has a different tactile impression than the rear wall. A resiliently compressible material is positioned within the housing. A pair of grips is attached to the housing such that each of the first and second lateral edges has one the grips attached thereto.

Another embodiment of the disclosure includes a housing configured for being placed on a person's body and having a front wall, a rear wall and a perimeter edge defined at a juncture of the front and rear walls. The perimeter edge includes a first lateral edge, a second lateral edge, a top edge and a bottom edge. Each of the front and rear walls is comprised of a flexible material. The front and rear walls each comprises a cloth material wherein the front wall has a different tactile impression than the rear wall. A resiliently compressible material is positioned within the housing.

Yet another embodiment of the disclosure provides for a method including positioning a cushion on a person's body such that the person can grip and view the cushion. The cushion includes a housing having a front wall, a rear wall and a perimeter edge defined at a juncture of the front and rear walls. The perimeter edge includes a first lateral edge, a second lateral edge, a top edge and a bottom edge. Each of the front and rear walls is comprised of a flexible material. The front and rear walls each comprise a cloth material. The front wall has a different tactile impression than the rear wall. A resiliently compressible material is positioned within the housing. The housing has a length from the first lateral edge to the second lateral edge is between 4.0 inches and 8.0 inches and a height from the bottom edge to the top edge between 3.0 inches and 6.0 inches. A pair of grips is attached to the housing. Each of the first and second lateral edges has one the grips attached thereto. A plurality of filaments is attached to and extends away from the top edge. A plurality of raised elements is attached to the housing. The raised elements are positioned only on the front wall.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 6 is a side in-use view of an embodiment of the disclosure.

DETAILED DESCRIPTION OF THE INVENTION

Figure 1:
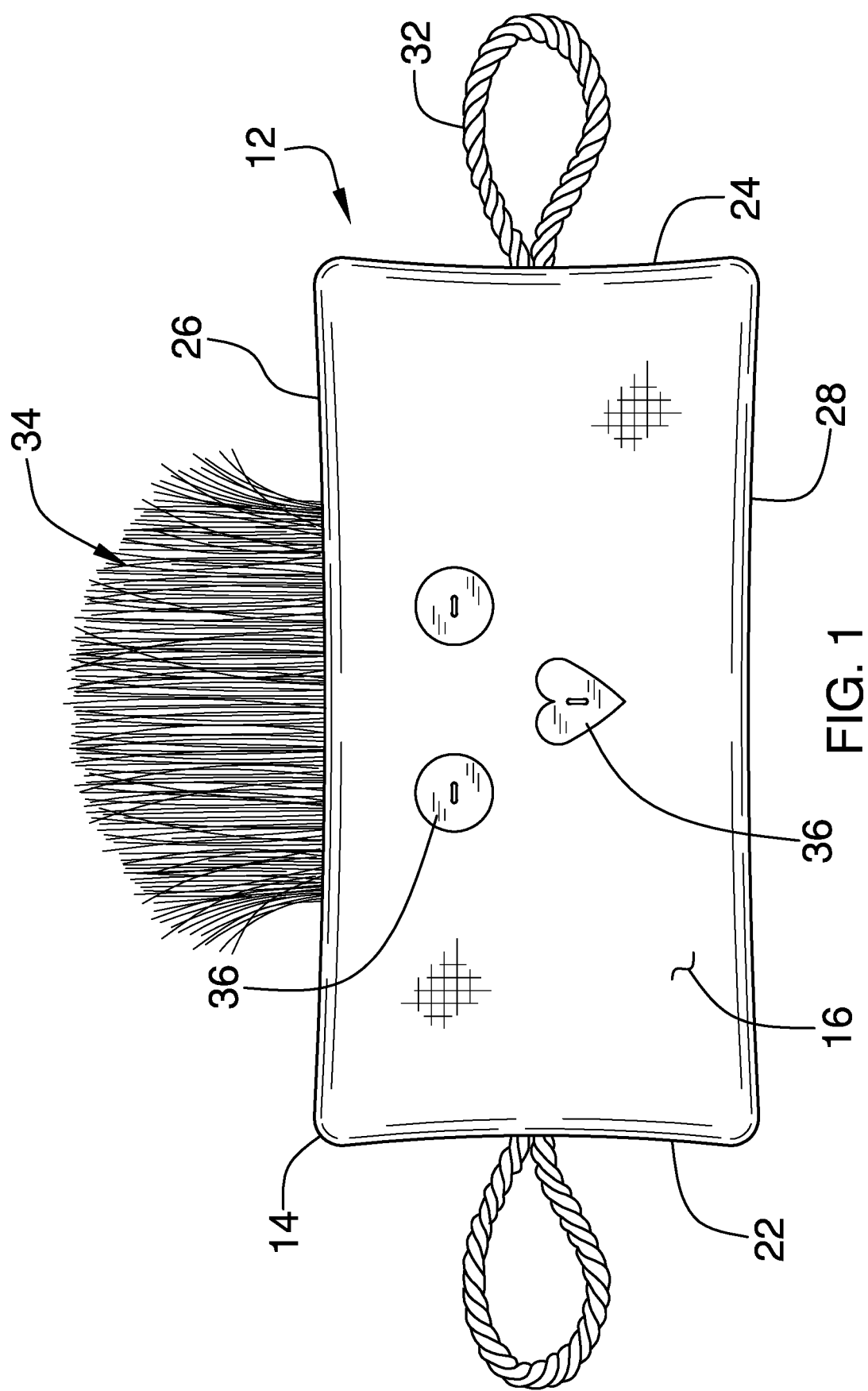
FIG. 1 is a front view of a mindfulness assisting assembly and method according to an embodiment of the disclosure.
Figure 2:
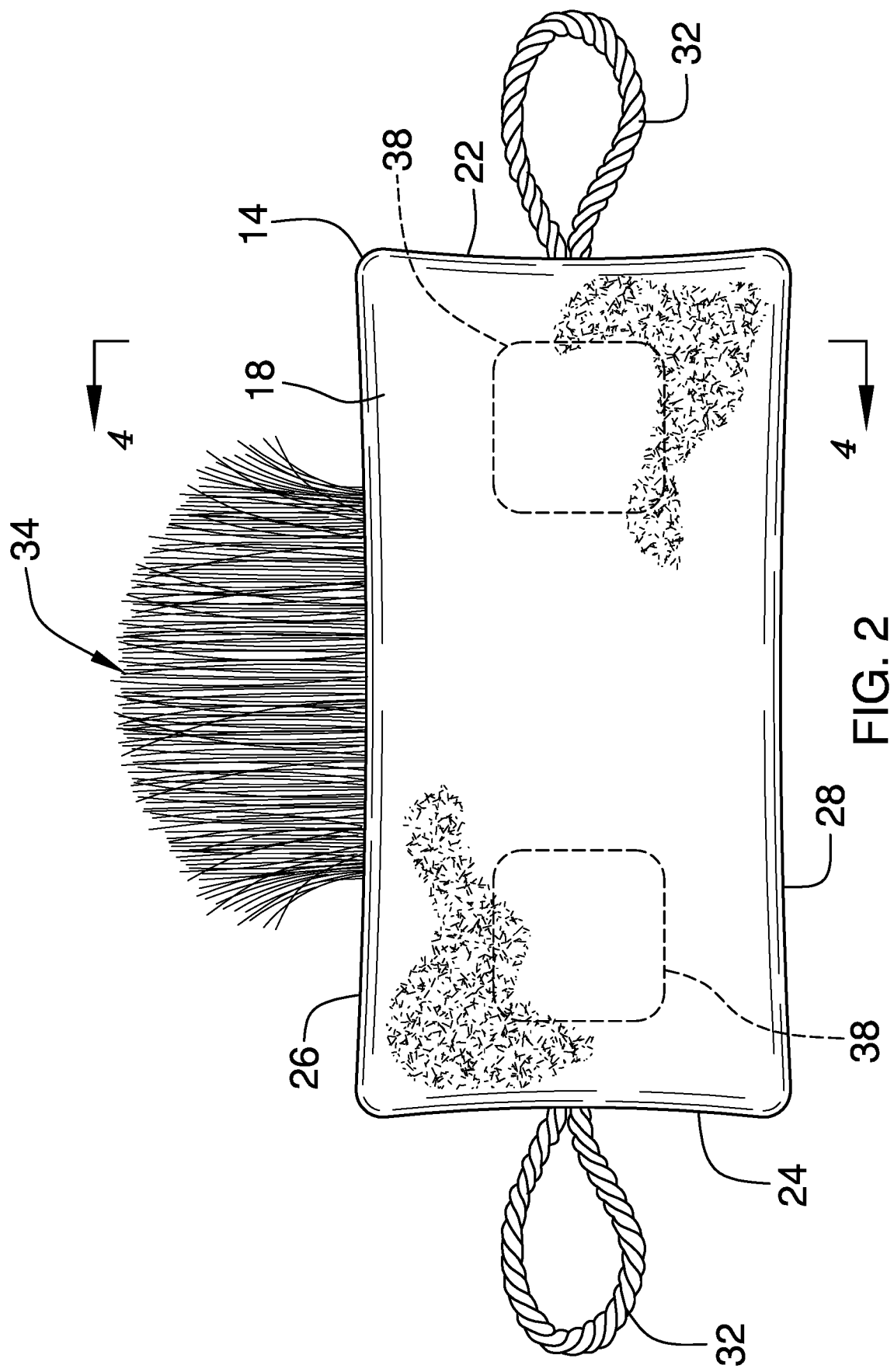
FIG. 2 is a rear view of an embodiment of the disclosure.
Figure 4:
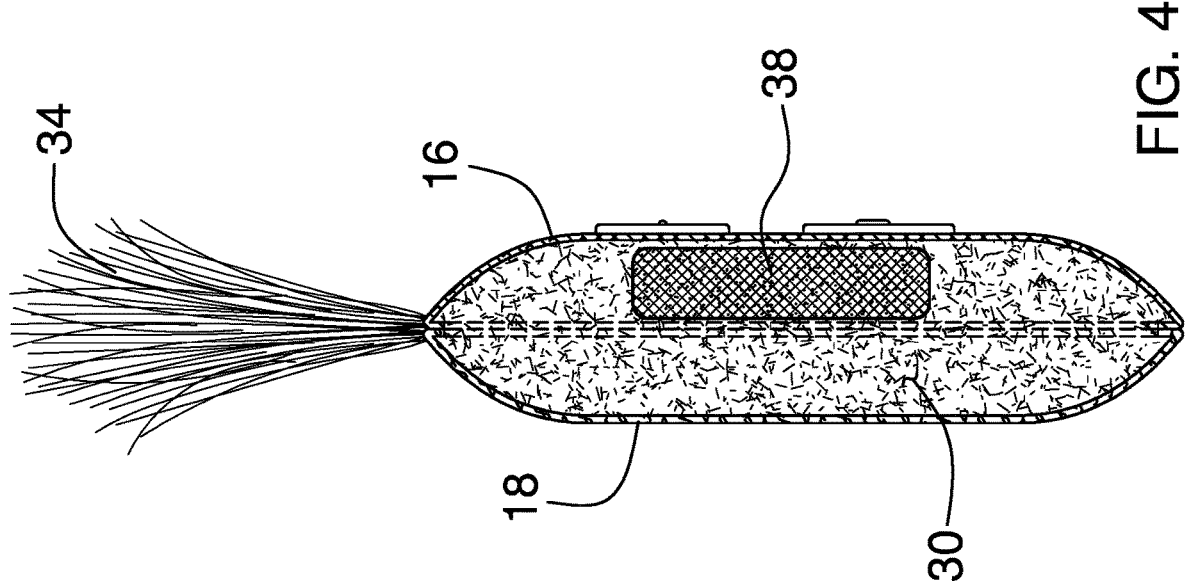
FIG. 4 is a cross-sectional view of an embodiment of the disclosure taken along line 4-4 of FIG. 2.
Figure 3:
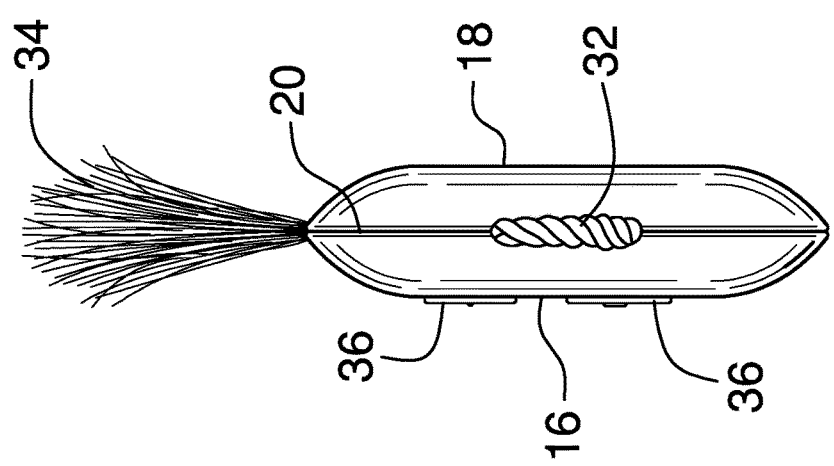
FIG. 3 is a side view of an embodiment of the disclosure.
Figure 5:
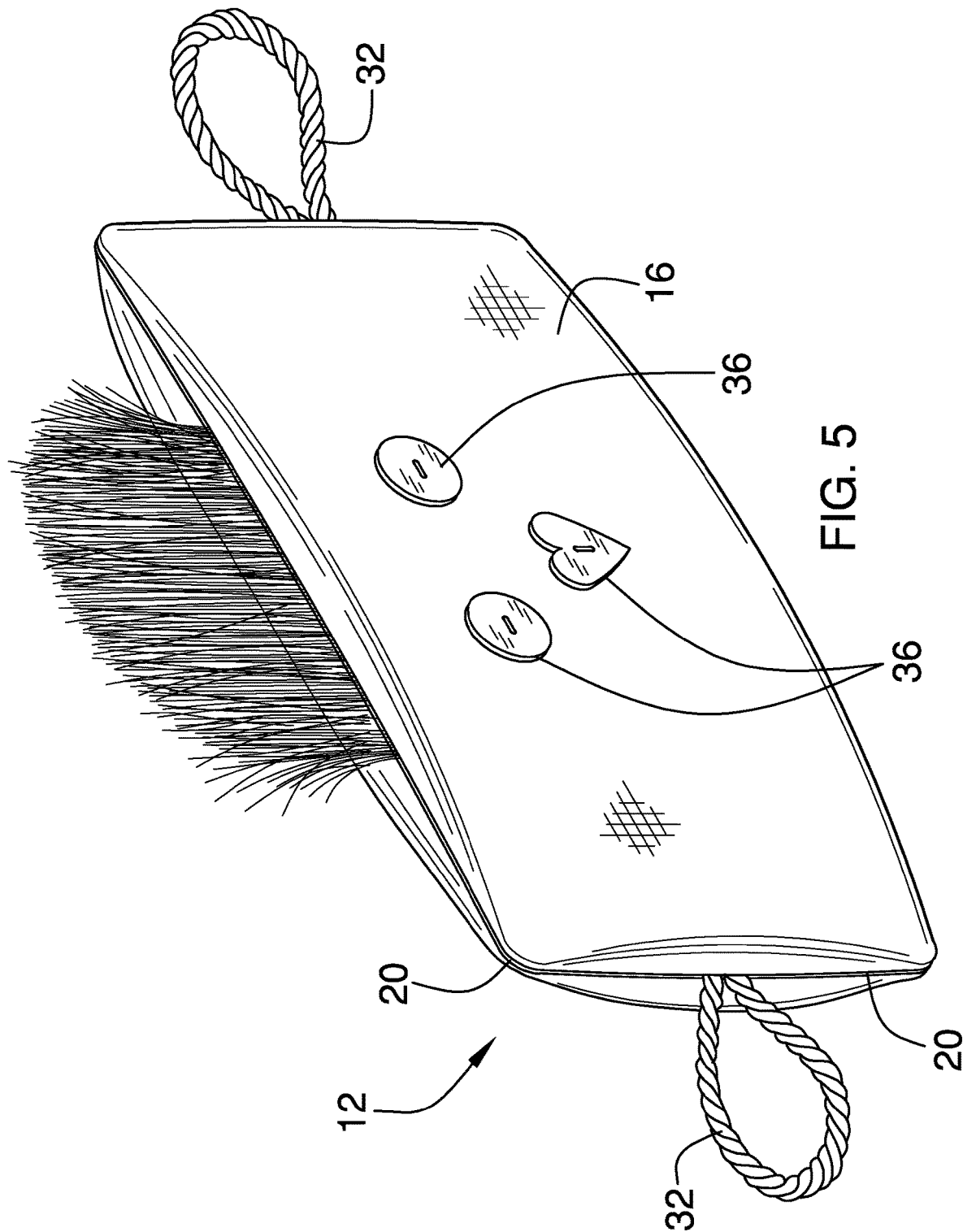
FIG. 5 is a top perspective view of an embodiment of the disclosure.

With reference now to the drawings, and in particular to FIGS. 1 through 6 thereof, a new meditation aid device embodying the principles and concepts of an embodiment of the disclosure and generally designated by the reference numeral 10 will be described.

As best illustrated in FIGS. 1 through 6, the mindfulness assisting assembly and method 10 generally comprises a cushion 12 construction that is positionable on a person's 70 body and in particular on the person's 70 stomach. However, it may also be placed over the person's 70 eyes to comfort and calm a person. The cushion 12 is grippable and viewable by the person 70, who may be a child, to assist the person 70 in maintaining mindful body and breath awareness. Specifically, the cushion 12 assists the person 70 to maintain focus on the present by focusing their attention on the multiple sensations provided by the cushion 12. Moreover, since the cushion 12 is viewable to the person 70, the cushion 12 provides visual feedback of the person's breathing pattern to aid in internal awareness. While an adult may more easily remain focused on their physical state, a child will more often have difficulty retaining focus for an adequate period of time. The tactile and visual feedback maintains the child's focus on their present state of physical and emotional wellbeing. Once this state is achieved, the child can learn to self-regulate their nervous system to sustain a calm state, increase focus and concentration, develop self-awareness, and encourage a sense of gratitude.

The cushion 12 comprises a housing 14 having a front wall 16, a rear wall 18 and a perimeter edge 20 defined at a juncture of the front 16 and rear 18 walls. The perimeter edge 20 includes a first lateral edge 22, a second lateral edge 24, a top edge 26 and a bottom edge 28. Each of the front 16 and rear 18 walls is comprised of a flexible material. The front 16 and rear 18 walls each comprise a cloth material wherein the front wall 16 has a different tactile impression than the rear wall 18. That is, for example, the front wall 16 may comprise a cotton cloth while the rear wall 18 may comprise a faux fur material. It should be understood that the front 16 and rear 18 walls may comprise any flexible material as long as the front 16 and rear 18 walls feel differently from each other. Generally, the rear wall 18 is comprised of a softer material than the front wall 16 so that the rear wall 18 may be positioned on the person's face without causing discomfort. A resiliently compressible material 30 is positioned within the housing and may comprise any material conventionally used for cushion or pillow stuffing.

The housing 14 has a length from the first lateral edge 22 to the second lateral edge 24 that is between 4.0 inches and 8.0 inches. The housing 14 has a height from the bottom edge 28 to the top edge 26 between 3.0 inches and 6.0 inches. The dimensions of the housing 14 are such that it will easily fit on a child's stomach or over their eyes without easily falling off thereof. Generally, the housing 14 will have a greatest depth from the front wall 16 to the rear wall 18 being less than 2.0 inches. These measurements may be modified, particularly if a version is produced which is much smaller and still provides the stimuli spoken of herein.

A pair of grips 32 is attached to the housing 14, though a single grip 32 may be contemplated. While the grips 32 may be positioned anywhere, it is preferred that each of the first 22 and second 24 lateral edges has one the grips 32 attached thereto. The grips 32 may comprise any type of grip or handle, though, as shown in the Figures, each of the grips 32 may comprise a loop wherein each of the grips comprises a flexible tether. The tether may be a corded tether comprised of a synthetic material or a cotton material, for example.

A plurality of filaments 34 is attached to and extends away from the top edge 26. The material used for the filaments 34 may vary as it is primarily important that they are of light weight and can be moved by the breath of a child as a child exhales onto the filaments 34 to cultivate breath awareness. These filaments 34 may be comprised, for example, of single strands of wool, feathers, other types of hair or synthetic strands having light weight properties and which are at least partially resiliently bendable such that they return to a shape extending outwardly from the housing 14.

A plurality of raised elements 36 is attached to the housing 14. The raised elements 36 allow a child to different structures on the housing 14 to maintain their attention on the housing 14. The raised elements 36 might only be positioned on the front wall 16. Moreover, as can be seen in the Figures, the raised elements 36 may be positioned to evoke an image. In the present case, the image is one of eyes and a nose or mouth. Additional features may be positioned on the front wall 16, which may or may not be raised, to further facilitate a chosen image. The raised elements 36 extend away from the surface of the front wall 16 and may comprise buttons attached to the front wall by thread, adhesive, chemical or heat bonding or other conventional attachment means. Embroidery may be substituted to form raised areas as well, and screen printing, for example, may be utilized for adding decorative elements which may not be easily felt as compared to buttons. However, raised elements 36 that extend more than 2.0 mm away from the front wall 16 of the housing 14 are preferred to ensure adequate tactile stimulation.

One or more scent pouches 38 are positioned within the housing 14 to stimulate the olfactory senses of the user of the assembly 10. Each scent pouch 38 emits a scent and the scent may comprise any chosen scent, though those scents, such as lavender, which promote relaxation may be preferred and therefore the scent pouch may be filled with dried lavender (*Lavandula spica*).

In use, the housing 14 is provided to a child while the child is attempting to calm their body and mind, such as during a meditation exercise or before bedtime. As children generally do not easily focus on their own emotions and feels, sometimes referred to as a "self-check", the assembly and method 10 provides personal feedback as to what their body is doing. The grips 32 and raised elements 36 provide tactile stimulation to assist in concentrating on the physical aspects of their current mood and to aid the child in promoting self-awareness. The filaments 34 provide visual cues as to the breathing of the child. Finally, the scent pouch 38 focuses the child to the present, meaning that their mind is not wandering onto a myriad of other subjects or thoughts, by providing a scent that constantly reminds the child of their current position within their surroundings. Taken together, the structure of the cushion 12 greatly enhances the ability of the child to remain in a present, focused state of mind which in turn substantially benefits their meditative efforts.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A tactile feedback assembly to assist a person in maintaining self-awareness and mindfulness, said assembly comprising:

a housing configured for being placed on a person's body and having a front wall, a rear wall and a perimeter edge defined at a juncture of said front and rear walls, said perimeter edge including a first lateral edge, a second lateral edge, a top edge and a bottom edge, each of said front and rear walls being comprised of a flexible material, said front and rear walls each comprising a cloth material, said front wall having a different tactile impression than said rear wall, a resiliently compressible material being positioned within said housing;

a pair of grips being attached to said housing, each of said first and second lateral edges having one of said pair of grips attached thereto at a respective center of said first and second lateral edges wherein said pair of grips are linearly aligned across said housing, wherein each of said grips comprises a loop; and a plurality of filaments being attached to said top edge, said plurality of filaments extending away from said top edge such that said plurality of filaments is extending away from said housing.

2. The tactile feedback assembly according to claim 1, wherein said housing has a length from said first lateral edge to said second lateral edge being between 4.0 inches and 8.0 inches, said housing having a height from said bottom edge to said top edge between 3.0 inches and 6.0 inches.

3. The tactile feedback assembly according to claim 1, wherein each of said grips comprises a flexible tether.

4. The tactile feedback assembly according to claim 1, further including a plurality of raised elements being attached to said housing.

5. The tactile feedback assembly according to claim 4, wherein said raised elements are positioned only on said front wall.

6. The tactile feedback assembly according to claim 5, wherein said raised elements comprise buttons.

* * * * *